(12) United States Patent
Estabrook et al.

(10) Patent No.: US 7,131,962 B1
(45) Date of Patent: Nov. 7, 2006

(54) PORT DEVICE FOR SUBCUTANEOUS ACCESS TO THE VASCULAR SYSTEM OF A PATIENT

(75) Inventors: Brian K. Estabrook, Foxboro, MA (US); Paul J. Smith, West Kingston, RI (US); Harold M. Martins, Newton, MA (US); Frank R. Prosl, Duxbury, MA (US)

(73) Assignee: ND Partners LLC, Boston, MA (US)

( * ) Notice: Subject to any disclaimer, the term of this patent is extended or adjusted under 35 U.S.C. 154(b) by 0 days.

(21) Appl. No.: 09/522,160

(22) Filed: Mar. 9, 2000

Related U.S. Application Data

(63) Continuation-in-part of application No. 08/661,903, filed on Jun. 12, 1996, now Pat. No. 6,013,058, and a continuation-in-part of application No. 09/226,956, filed on Jan. 8, 1999, now Pat. No. 6,013,058.

(60) Provisional application No. 60/123,432, filed on Mar. 9, 1999.

(51) Int. Cl.
*A61M 31/00* (2006.01)

(52) U.S. Cl. .................................................. 604/93.01
(58) Field of Classification Search ........... 604/288.01, 604/175, 264, 288.02, 288.03, 288.04, 93.01, 604/523, 533–535; 285/323, 322
See application file for complete search history.

(56) References Cited

U.S. PATENT DOCUMENTS

| | | | | |
|---|---|---|---|---|
| 4,895,570 A | * | 1/1990 | Larkin | .................. 604/411 |
| 4,923,220 A | * | 5/1990 | Guest et al. | .................. 285/39 |
| 5,527,277 A | * | 6/1996 | Ensminger et al. | ......... 604/116 |
| 5,911,706 A | * | 6/1999 | Estabrook et al. | ......... 604/116 |

\* cited by examiner

*Primary Examiner*—LoAn H. Thanh
(74) *Attorney, Agent, or Firm*—Burns & Levinson LLP; Frederick C. Williams; Kimberly B. Whitehead

(57) ABSTRACT

A port device for implanting in a patient for subcutaneous access to the vascular system of the patient. The device includes a housing provided with apertures, each for receiving and retaining a needle. The housing is further provided with lock structure for locking catheters to the housing. The housing is configured internally to provide flow paths extending between needles disposed in the apertures and the catheters.

1 Claim, 18 Drawing Sheets

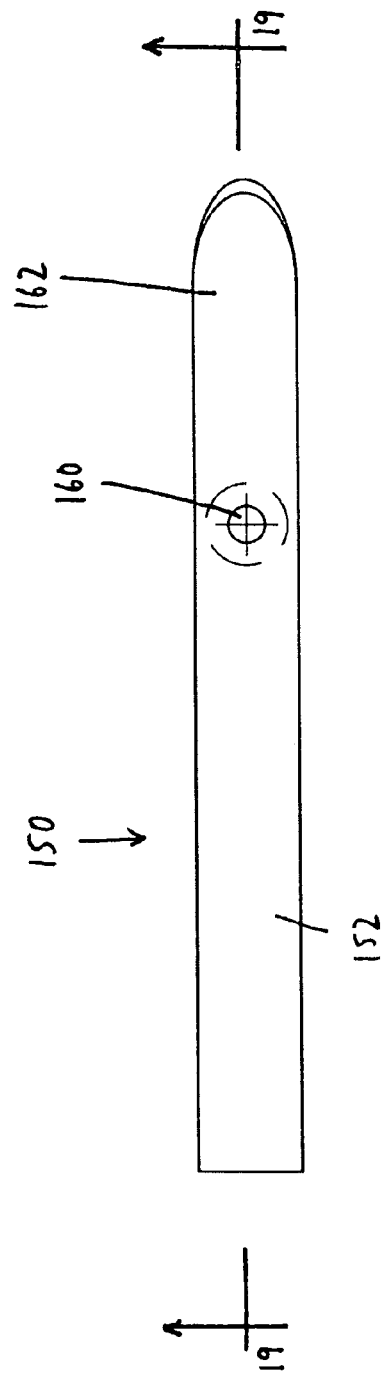
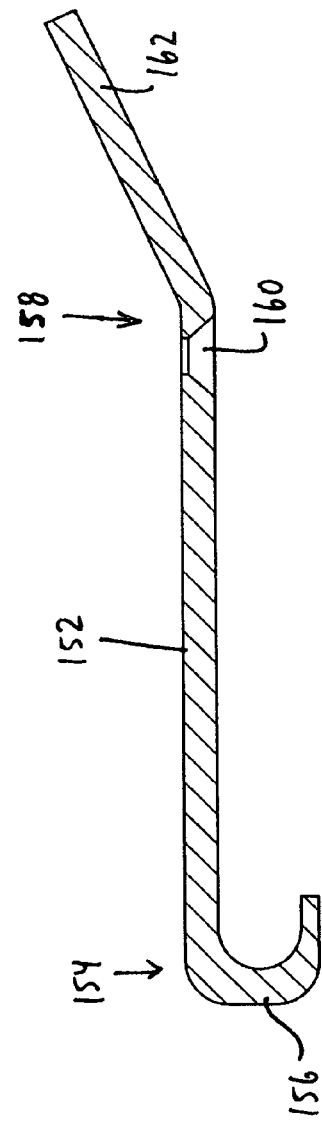
FIG. 18
FIG. 19

PORT DEVICE FOR SUBCUTANEOUS ACCESS TO THE VASCULAR SYSTEM OF A PATIENT

REFERENCE TO PENDING PRIOR PATENT APPLICATIONS

This application claims the benefit of (1) pending prior U.S. Provisional Patent Application Ser. No. 60/123,432, filed Mar. 9, 1999 by Brian K. Estabrook et al. for SUBCUTANEOUS HEMODIALYSIS ACCESS PORT AND METHOD OF USING SAME, and (2) is a continuation-in-part of U.S. patent application Ser. No. 09/226,956, filed Jan. 8, 1999 by Brian K. Estabrook et al. for APPARATUS AND METHOD FOR SUBCUTANEOUS ACCESS TO THE VASCULAR SYSTEM OF A PATIENT, now U.S. Pat. No. 6,506,182, which in turn is a continuation-in-part of U.S. patent application Ser. No. 08/661,903, filed Jun. 12, 1996 by Brian K. Estabrook et al. for DEVICE FOR SUBCUTANEOUS ACCESSIBILITY, now U.S. Pat. No. 6,013,058.

The disclosures of the aforementioned three (3) U.S. patent applications are hereby incorporated herein by reference.

FIELD OF THE INVENTION

The present invention relates generally to an apparatus that allows access to the vascular system of a human (or animal), and particularly for the high-volume fluid flow required in hemodialysis, plasmapheresis, and other fluid exchange therapies. More particularly, the present invention relates to a subcutaneously-implantable access device.

BACKGROUND OF THE INVENTION

There exists a class of devices for accessing fluid spaces and vessels within a human (or animal) body that are generally referred to as "ports". Herein, "vessel" is defined as any conduit carrying a fluid within the patient's body. These prior art port devices generally comprise a chamber having an access opening sealed by means of a septum and having an egress from a second location leading to a catheter which is disposed within a fluid space or vessel. The septum allows a hollow needle (or "cannula") to pass into the port's chamber, but then closes when the needle is removed, thereby preventing fluid leakage from within the bodily fluid space or vessel and also preventing anything from entering or exiting the port's chamber. These port devices are usually implantable below the skin so as to prevent infection, other contamination and mishandling.

A problem associated with prior art port devices is that they tend to have a somewhat irregular external shape. This can create various problems. For one thing, it can make it harder for the body to form a fibrin pocket about the port after the port has been installed below the skin. Furthermore, when the port has been deployed in the body for a prolonged period of time, the irregular external shape of the port can cause undesirable tissue erosion.

Another problem associated with prior art ports is that it can be difficult for medical personnel to locate a port beneath the patient's skin. Additionally, even after being located, it can be difficult for medical personnel to identify the orientation of the port within the body. This makes it more difficult for the medical personnel to find the port's needle (or cannula) entrances.

Still another problem associated with prior art ports is that, even after knowing the orientation of the port within the body, it can be difficult for medical personnel to insert the hemodialysis needles (or cannulas) in the needle (or cannula) entrances. In many cases, medical personnel strike the adjoining casing of the port, or pass the needle beneath the port.

Yet another problem associated with prior art ports is that it can be difficult to connect and disconnect catheters to the ports. For one thing, it can be difficult to securely lock the catheters to the ports. And, once locked, it can be difficult to thereafter unlock the catheters from the ports. In addition, some new catheters use coil-reinforced constructions. Such coil-reinforced catheters can be incompatible with prior art ports.

SUMMARY OF THE INVENTION

It is, therefore, an object of the invention to provide a port device having a smooth, generally rounded configuration, lessening the likelihood of erosion of surrounding tissue and lessening impeding of formation of a fibrin pocket around the implanted device.

Another object of the invention is to provide a port device having an outboard tactile surface by which a surgeon, through feel of the surface residing beneath the skin, can substantially determine the location and orientation of the needle entrances of the device, so as to properly direct a needle or cannula (hereinafter "needle") through the skin in the direction of the device's needle entrances.

A still further object of the invention is to provide such a port device with needle receiving surfaces adapted to guide a needle into a needle entrance.

Still another object of the invention is to provide such a port device with means for securely locking catheters, of the type reinforced by coils of metal wire, to the port device, and means for effecting separation of the catheters from the device when desired.

Another object of the invention is to provide such a port device having means thereon to facilitate suturing of the device to tissue.

A still further object of the invention is to provide a port device which is useful for other liquid or fluid (including gases) transfer purposes into and out of human and animal bodies, including the transfer of externally-prepared solutions for cleaning, flushing, dialysis, chemical agent delivery, transfusions, blood donation, insufflation, wound drainage, and the like.

With the above and other objects in view, as will hereinafter appear, a feature of the present invention is the provision of a port device for implanting in a patient for subcutaneous access to the vascular system of the patient. The device includes a housing having needle receiving apparatus, and apparatus for connecting a catheter to the housing, the housing being adapted to provide a flow path extending between a needle disposed in the needle receiving apparatus and the catheter. The housing defines a groove therein for positioning under and adjacent the skin of the patient. The groove is of sufficient tactility to convey to an operator the subcutaneous location and orientation of the housing.

In accordance with a further feature of the invention, there is provided a port device for implanting in a patient for subcutaneous access to the vascular system of the patient. The device includes a housing having needle receiving apparatus, and apparatus for connecting a catheter to the housing, the housing being adapted to provide a flow path extending between a needle disposed in the needle receiving apparatus and the catheter. The housing defines a raised surface, aligned with the needle receiving apparatus, for positioning under and adjacent the skin of the patient. The raised surface is of sufficient tactility to convey to an operator the subcutaneous location of the needle receiving apparatus.

In accordance with another feature of the invention, there is provided a port device for implanting in a patient for subcutaneous access to the vascular system of the patient. The device includes a housing having needle receiving apparatus, and apparatus for connecting a catheter to the housing, the housing being adapted to provide a flow path extending between a needle disposed in the needle receiving apparatus and the catheter. The needle receiving apparatus includes an opening in the housing and in communication with the flow path. The housing defines needle guiding surfaces for guiding the needle from a first location removed from the opening to a second location coincident with the opening.

In accordance with a still further feature of the invention, there is provided a device for implanting in a patient for subcutaneous access to the vascular system of the patient. The device includes a housing having needle receiving apparatus, and apparatus for connecting a catheter to the housing. The housing is adapted to provide a flow path extending between a needle disposed in the needle receiving apparatus and the catheter. The housing defines a ledge within a profile of the housing and having a suture orifice therein and extending therethrough.

In accordance with a further feature of the invention, there is provided a port device for implanting in a patient for subcutaneous access to the vascular system of the patient. The device includes a housing having needle receiving apparatus, and apparatus for connecting a catheter to the housing, the housing being adapted to provide a flow path extending between a needle disposed in the needle receiving apparatus and the catheter. The housing is provided with a smooth, generally rounded exterior.

In accordance with a further feature of the invention, there is provided a port device for implanting in a patient for subcutaneous access to the vascular system of the patient. The device includes a housing having needle receiving apparatus, and lock means for locking a catheter to the housing. The lock means includes a collet for receiving the catheter when the collet is in an open condition, and a lock member responsive to application of a cam means to close the collet with the catheter therein, whereby to lock the catheter in the collet and thereby in the housing.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

The above and other objects and features of the present invention will be more fully disclosed or rendered obvious by the following detailed description of the preferred embodiment of the invention, which is to be considered together with the accompanying drawings wherein like numbers refer to like parts, and further wherein:

FIG. 18 is an elevational view of an unlocking tool for use in unlocking catheters for separation from the port device;

FIG. 19 is a sectional view taken along line 19—19 of FIG. 18;

DESCRIPTION OF THE PREFERRED EMBODIMENT

Figure 1:
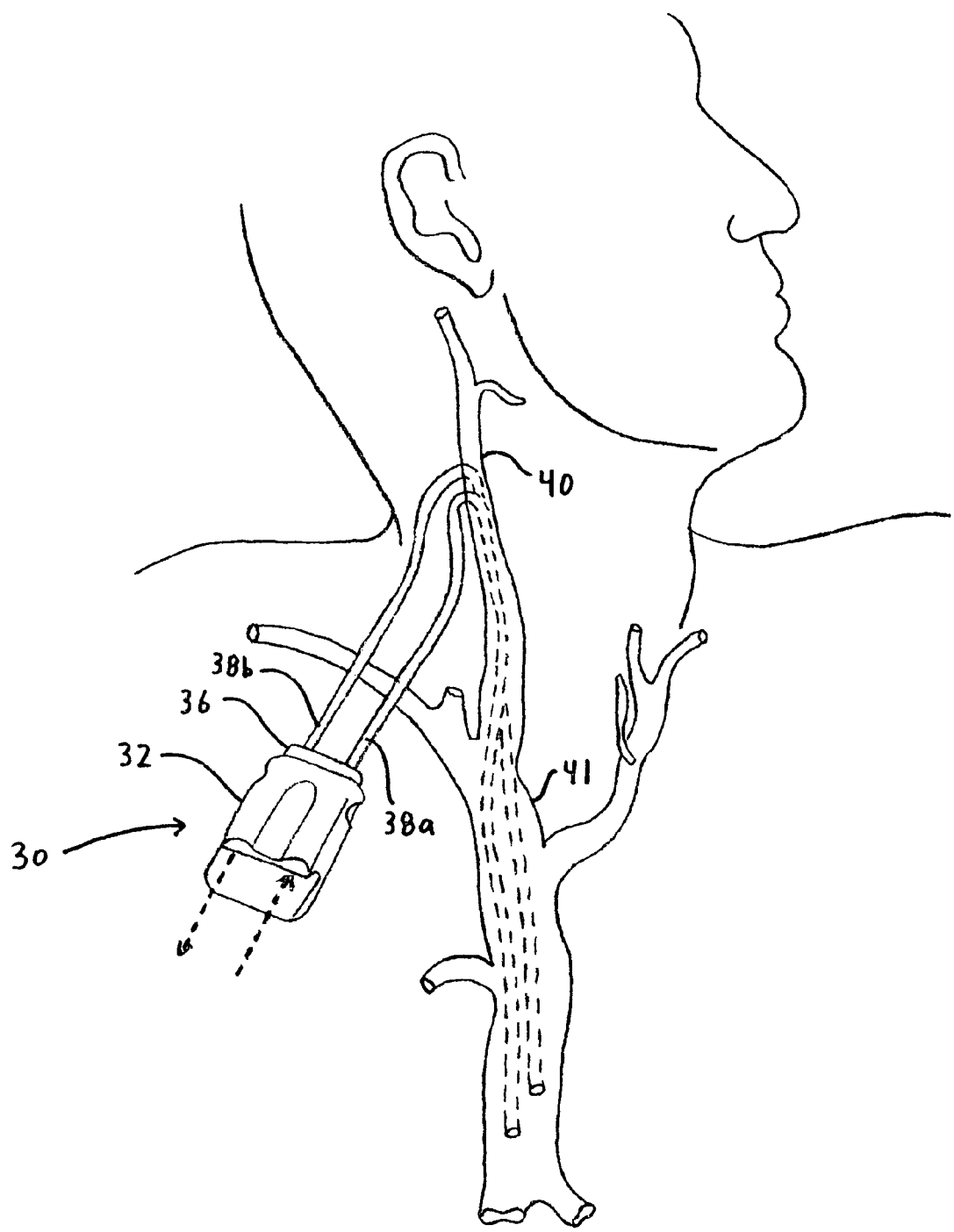
FIG. 1 is a diagrammatic view of one form of port device illustrative of an embodiment of the invention, shown in use.
Figure 2:
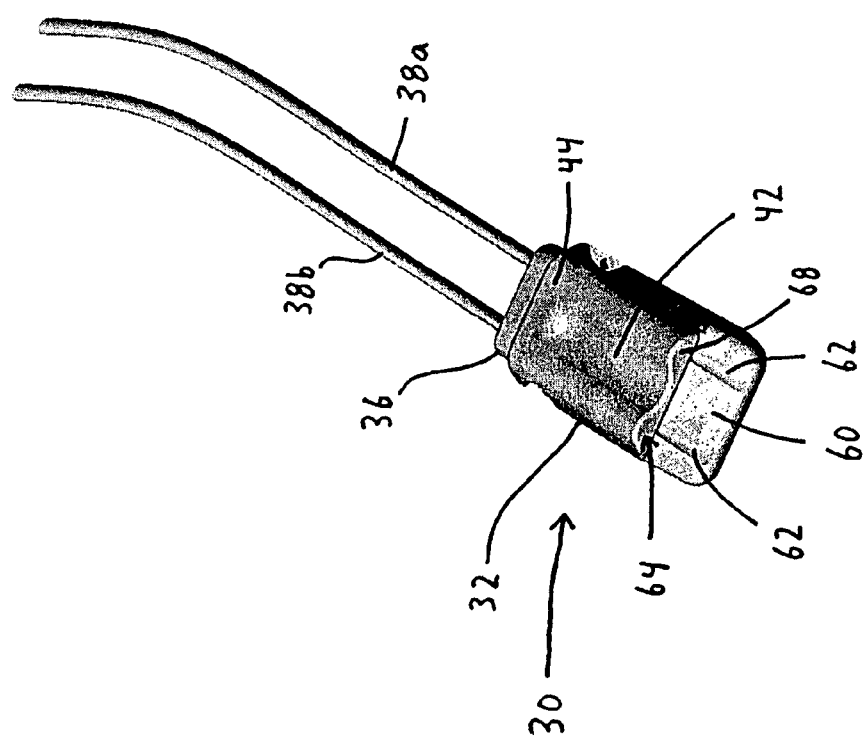
FIG. 2 is a perspective view of the illustrative port device.
Figure 3:
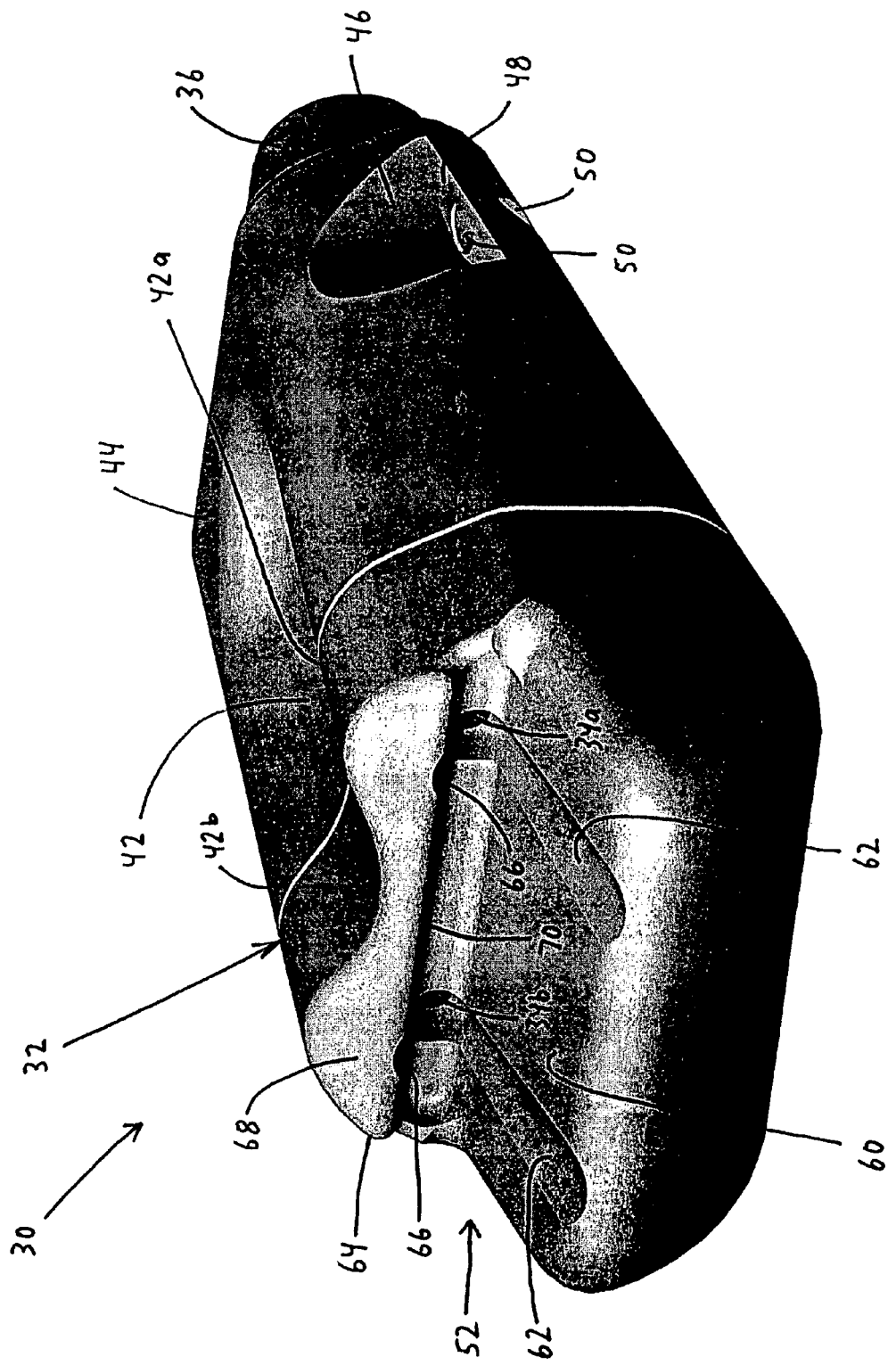
FIG. 3 is a perspective view of the port device of FIGS. 1 and 2.

Referring to FIGS. 1–3, it will be seen that the port device 30 of the present invention is adapted to be disposed subcutaneously in the body of a patient, usually in the chest region. The device includes a housing 32 having a pair of needle entrances 34a, 34b which are accessed subcutaneously by a pair of needles (not shown) connected to conduits (not shown) for flowing fluid, such as blood, from the housing 32 and to the housing. In the aforementioned U.S. patent application Ser. No. 09/226,956, incorporated herein by reference, various configurations and arrangements of needles are discussed in detail.

The housing 32 is provided with means for retaining the needles and with flow paths for channeling the flow therethrough of fluid received from, and directed toward, the needles, as discussed in detail in the '956 patent application.

The port device 30 further includes lock means 36 for securely fixing to the housing 32 a pair of catheters 38a, 38b which may, in one application of the invention, extend through the jugular vein 40 of the patient, down the superior vena cava 41, and to a point in or near the right atrium of the heart of the patient. A first one 38a of the catheters receives the flow of blood, or other selected fluid (hereinafter "blood") from the housing 32 and directs the blood to the patient, while the other one 38b of the catheters flows blood from the patient and into the housing 32, or vice versa. As noted above, the housing 32 is provided with flow paths therethrough for flowing the blood in opposite directions. The housing 32 typically is in communication with a dialysis machine, or the like, which receives blood from one 34b of the needle entrances by a needle and blood line connection (not shown), and discharges blood to the other 34a of the needle entrances by another needle and blood line connection (not shown).

As shown in FIGS. 2–4 and 6, the housing 32 is provided with a smooth, generally rounded exterior, or profile. As may be seen in FIG. 4, the profile is of a generally tear-drop configuration. The smooth rounded profile, devoid of sharp edges, accommodates to surrounding tissue and enables the tissue to more readily form a fibrin pocket around the device while minimizing erosion of surrounding tissue.

Figure 6:
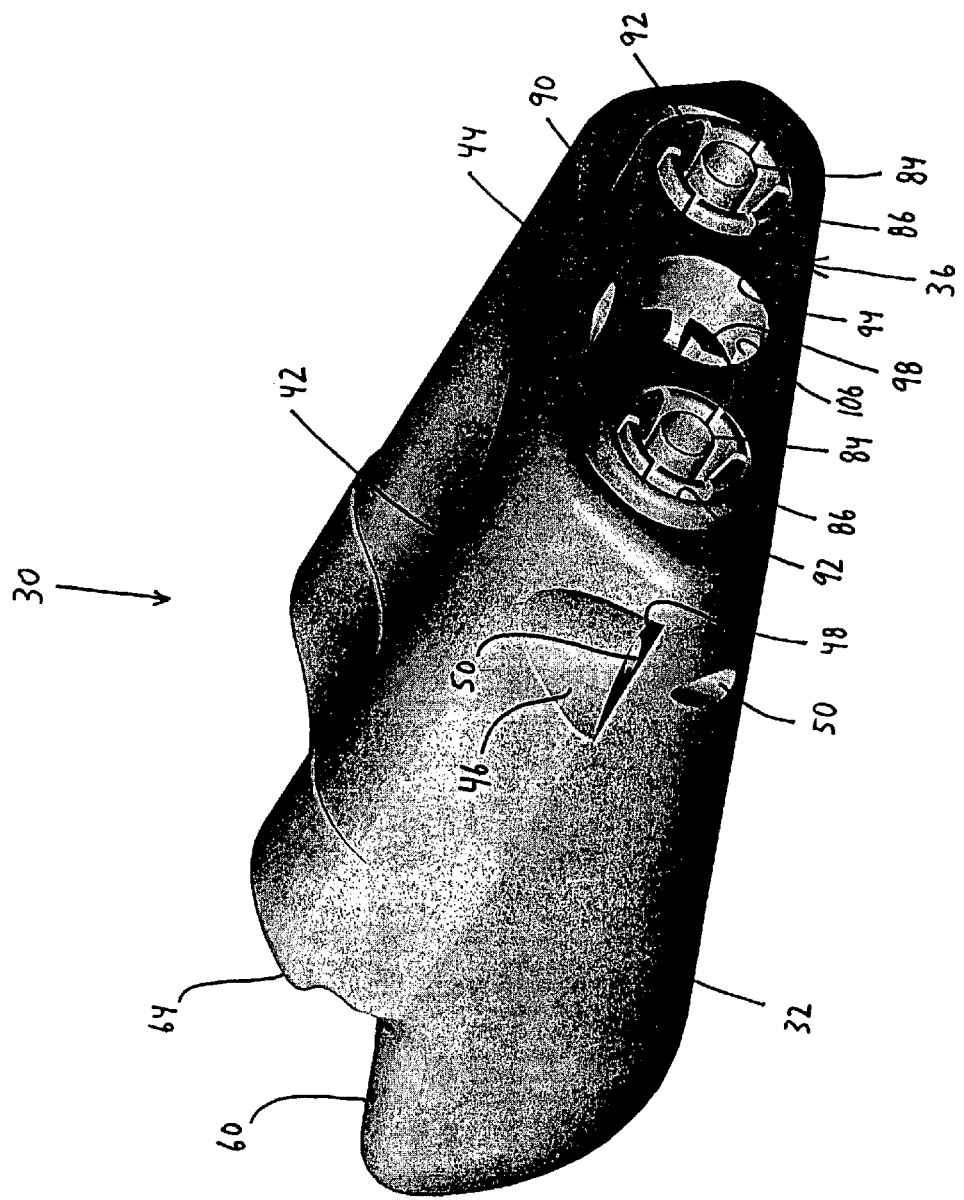
FIG. 6 is a further perspective view of the port device, showing a catheter locking feature.

In FIGS. 2, 3 and 6, there is shown an axially-extending gently sloped groove 42 in a surface 44 of the housing 32 which, when the device is embedded in a patient, lies beneath and adjacent the patient's skin. In keeping with the smooth, rounded profile of the device 30, the groove 42 is of rounded configuration, devoid of sharp or pronounced edges. The groove 42, however, is appropriately distinct to provide sufficient tactility to convey by "feel" to an operator the subcutaneous location and orientation of the housing 32. In addition, raised surfaces 42a, 42b are preferably formed on either side of groove 42, in alignment with needle openings 34a, 34b, whereby the operator can locate, by "feel", the position of needle openings 34a, 34b. Thus, before passing needles through the patient's skin, the operator may feel the surface 44 of the device 30 through the skin, and feel the groove 42 to determine the location in which the device is disposed and the orientation of the device, and feel the raised surface 42a, 42b so as to determine approximately the location of the openings 34a and 34b. This enables the first penetration to place the needles in the vicinity of the needle openings, without repeated penetrations which can be disconcerting to the patient.

Figure 4:
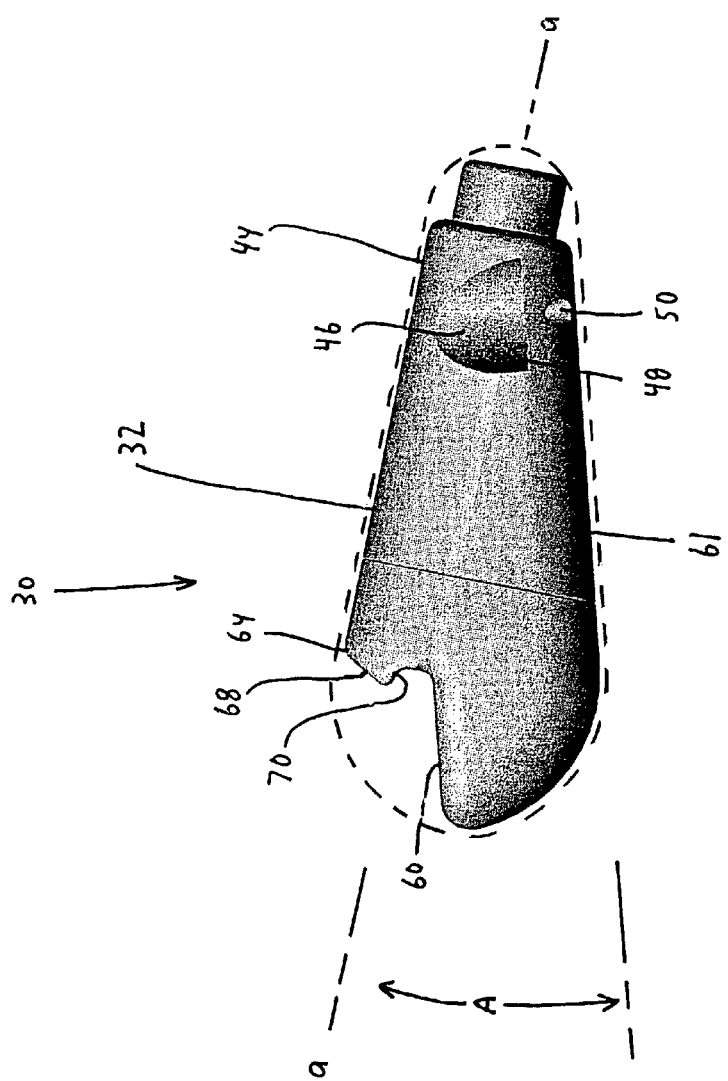
FIG. 4 is a side elevational view thereof.

Referring to FIG. 3, it will be seen that the device 30 is provided with needle receiving means 52 including the openings 34a, 34b, and including a needle guiding surface, or a "front porch", 60. The axis a—a of the needle openings 34a, 34b extend at an angle A to the base surface 61 of port 30 (FIG. 4). The angle A is preferably less than about 30°, and preferably is about 15°. The front porch 60 is also provided with guiding grooves 62, each aligned with one of the needle openings 34a, 34b. Extending over a portion of the front porch 60 is an overhang 64 in part constituting a portion of the surface 44 and having therein a portion of the groove 42. The overhang 64 is provided with guiding grooves 66, each aligned with one of the needle openings 34a, 34b. In keeping with the smooth, rounded configuration of the housing 32, the front porch 60 and overhang 64 are of smooth and rounded configuration.

Figure 5:
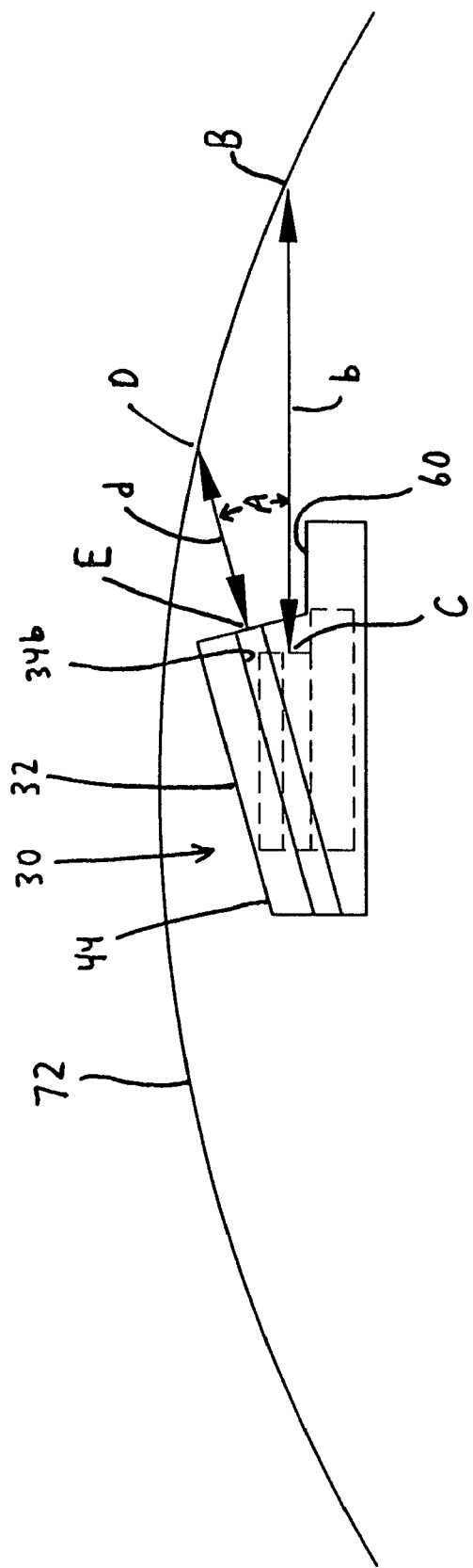
FIG. 5 is a side diagrammatic view of the port device showing preferred positioning and attitude of the device.

In FIG. 5, there is illustrated diagrammatically a preferred disposition of the device 30 in a body. In the port devices of the prior art, shown in FIG. 5 in phantom, the axes of the needle openings are generally parallel with the top and bottom surfaces of the port device, which are parallel to each other. To gain entrance of a needle into the needle opening 34b, it is necessary to penetrate the skin 72 at point B and move the needle distal end to point C, a distance represented by arrow b in FIG. 5. Using the port device as disclosed herein, the skin 72 is penetrated at point D and the needle distal end is moved to point E, a distance represented by the arrow d, substantially shorter than distance b. The shorter distance d reduces discomfort to the patient and permits use of shorter needles which, in turn, increases flow rate.

In addition, the needle receiving means 52, other than the apertures 34a, 34b themselves, assist in guiding needles to the openings 34a, 34b. Returning to FIG. 3, it will be seen that a needle striking the front porch 60 can be slid along the porch until the guiding grooves 62 are encountered. Needles may then follow along the guiding grooves 62 until the needles arrive at the needle openings 34a, 34b. Similarly, if the needles are aimed too high, they will encounter a forward surface 68 and may be slid along the surface 68 to an undersurface 70, and then to the guiding grooves 66 and the needle openings 34a, 34b.

Accordingly, by use of the locating groove 42 and the raised surfaces 42a, 42b, an operator may determine the general location of the needle openings 34a, 34b. By placing the penetrating needles in the correct location, the operator will generally move the needles into the needle receiving means 52, which help guide the needles into the needle openings 34a, 34b.

Referring to FIGS. 3, 4, 6 and 7, it will be seen that the device housing 32 is provided with recesses 46, each formed in part by a ledge 48 having an orifice 50 extending therethrough. The orifices 50 facilitate suturing of the device 30 to tissue in the body, to hold the device in a selected location. The recesses 46 and ledges 48 are within the housing profile, that is, the ledges 48 are wholly within the smooth and rounded boundary of the housing, so as to minimize irritation and/or erosion of the surrounding tissue.

Figure 7:
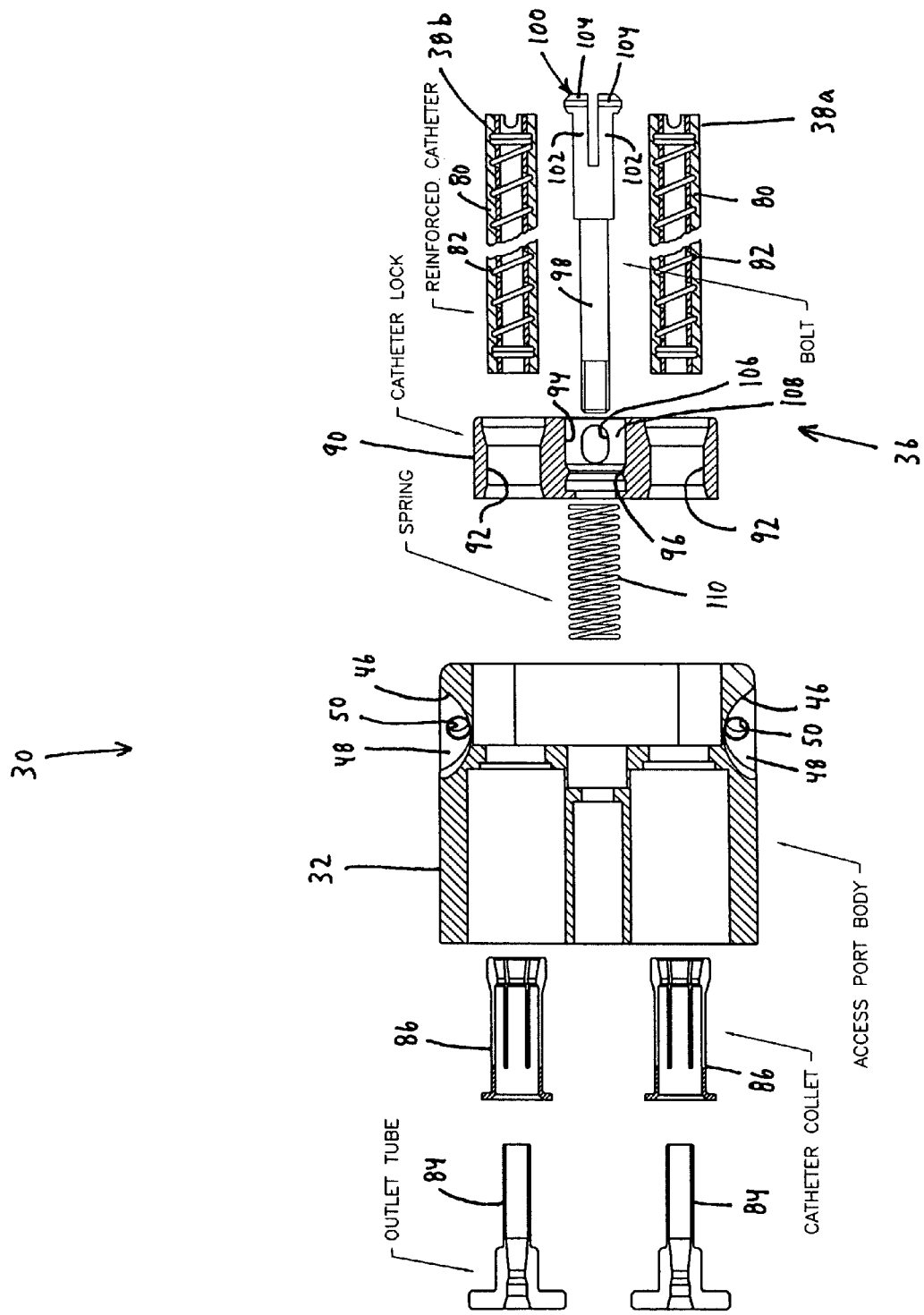
FIG. 7 is a generally sectional exploded view of the device.
Figure 8:
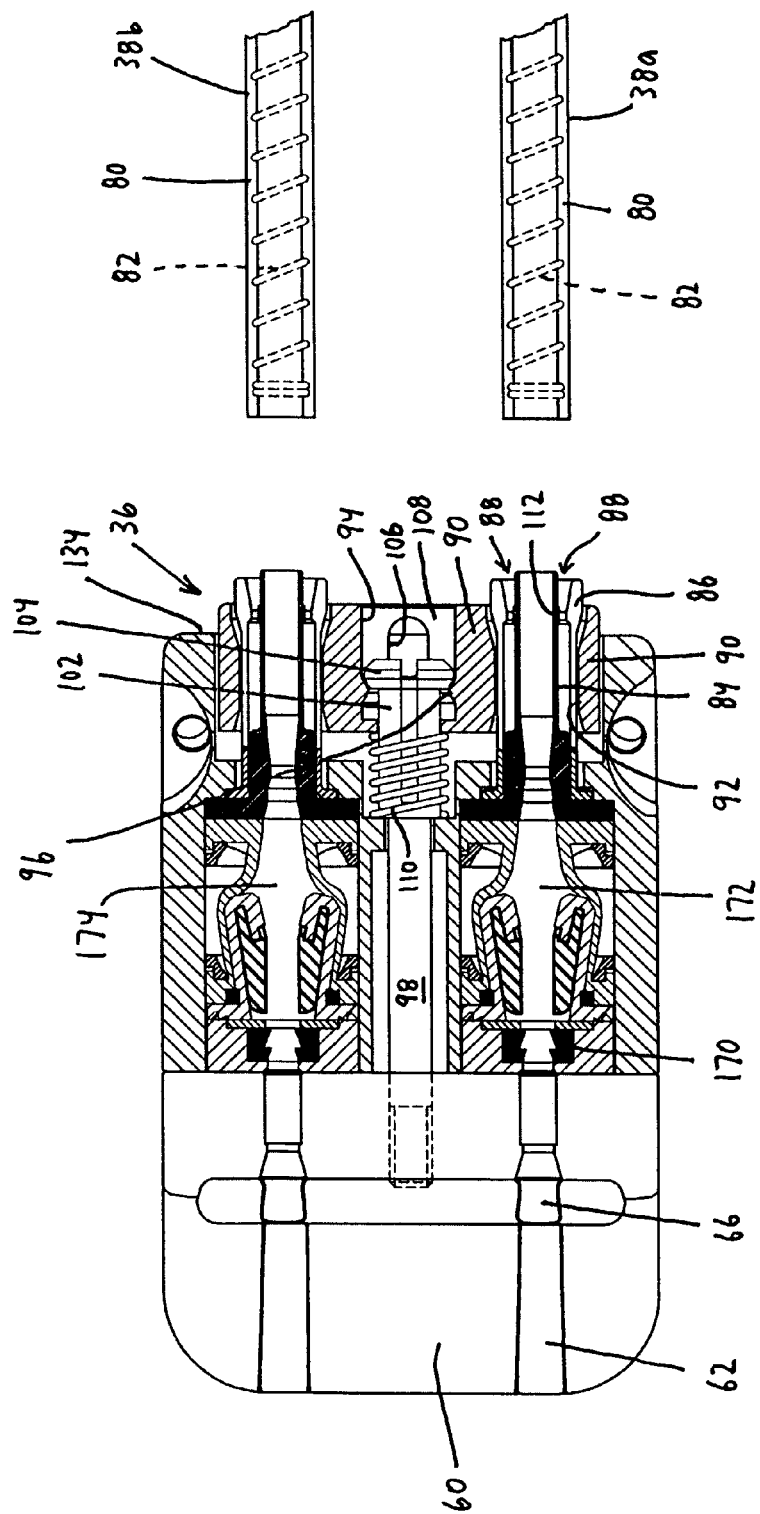
FIG. 8 is a generally sectional view of the device.
Figure 12:
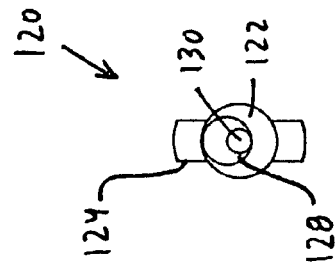
FIG. 12 is a camming end view thereof.
Figure 9:
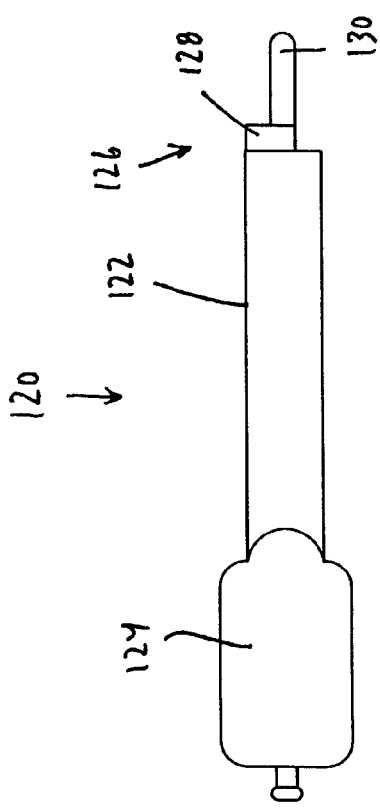
FIG. 9 is a front elevational view of a locking tool for use in locking catheters to the port device.
Figure 10:
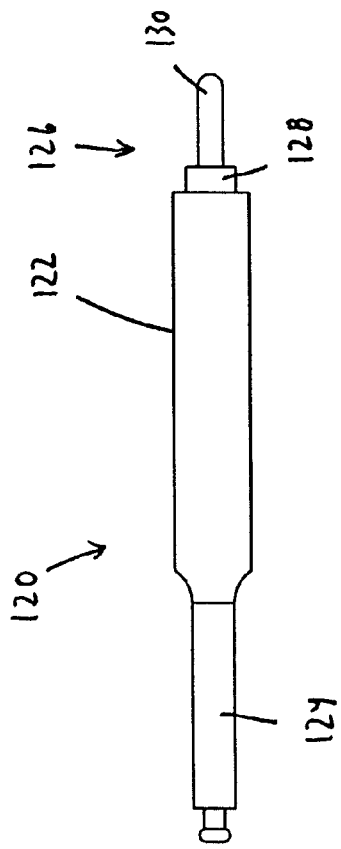
FIG. 10 is a side elevational view thereof.
Figure 11:
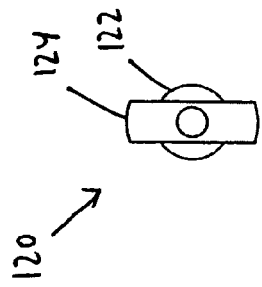
FIG. 11 is a handle end view thereof.

In FIGS. 7 and 8, there is shown the lock means 36 for locking to the housing 32 the pair of reinforced catheters 38a, 38b. The catheters 38a, 38b each include a flexible elastomeric tube 80 reinforced by a wire coil 82. The reinforced catheter is shown and described in U.S. patent application Ser. No. 09/251,572, filed Feb. 17, 1999 by Harold M. Martins et al. for APPARATUS FOR THE DIALYSIS OF BLOOD, METHOD FOR FABRICATING THE SAME, AND METHOD FOR THE DIALYSIS OF BLOOD, the disclosure of which is hereby incorporated herein by reference.

In the housing 32, there are provided outlet tubes 84 fixed in the housing, as shown in FIG. 8. The lock means 36 include a collet 86 disposed around each of the outlet tubes 84. Annular spaces 88 are defined by the tubes 84 and collets 86. A lock member 90 is provided with bores 92, each for housing a collet 86 and tube 84. The lock member 90 is further provided with a third bore 94 having therein an annular ridge 96. A locking bolt 98 is fixed at its proximal end in the housing 32 and extends through the bore 94. The bolt 98 is bifurcated at its distal end 100 (FIG. 7) to provide spaced apart opposed leg portions 102 of the bolt 98, each having a radially extending flange 104 at its distal end. The bore 94 is provided with a slot 106 in a side wall 108 thereof. In FIG. 8, it will be seen that a coil spring 110 is mounted in the housing 32 and urges the lock member 90 distally on the fixed locking bolt 98.

In the condition shown in FIG. 8, the lock member annular ridge 96 is urged by the spring 110 into engagement with the lock bolt flange 104, which normally prevents further distal movement of the lock member 90. FIG. 8 shows the catheters 38a, 38b removed from the housing 32, the lock means 36 unlocked, and the annular spaces 88 open.

A locking tool 120 for use in conjunction with the port device lock means 36 is shown in FIGS. 9–12 and includes a rod 122 and a handle 124 fixed thereto. At the distal end 126 of the rod 122 is fixed an eccentric circular cam portion 128. Extending axially from the cam portion 128 is a pin portion 130 which may be centered with respect to the rod 122.

Figure 13:
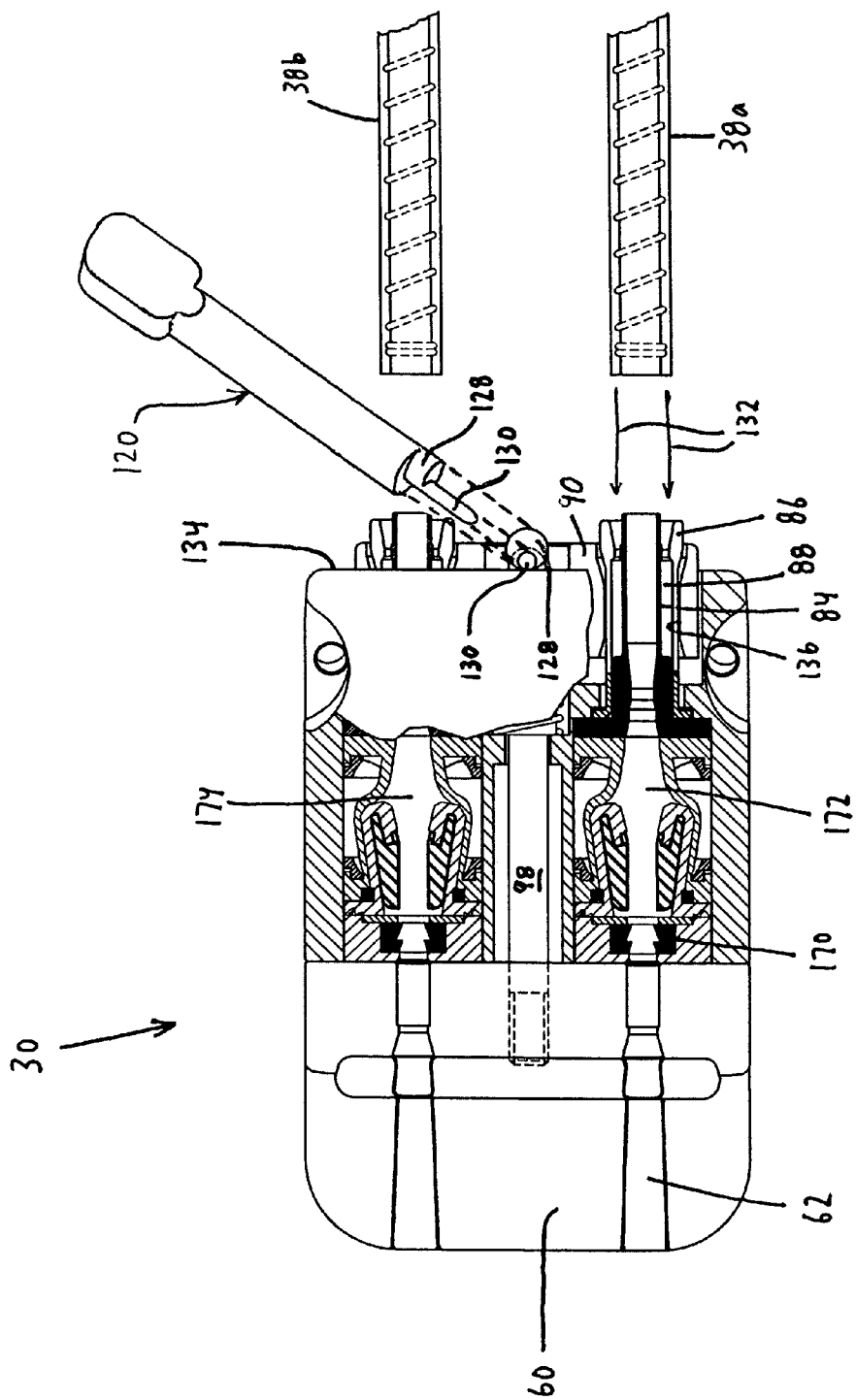
FIG. 13 is a broken away, generally sectional view of the device with the locking tool of FIGS. 9–12 shown in perspective.
Figure 14:
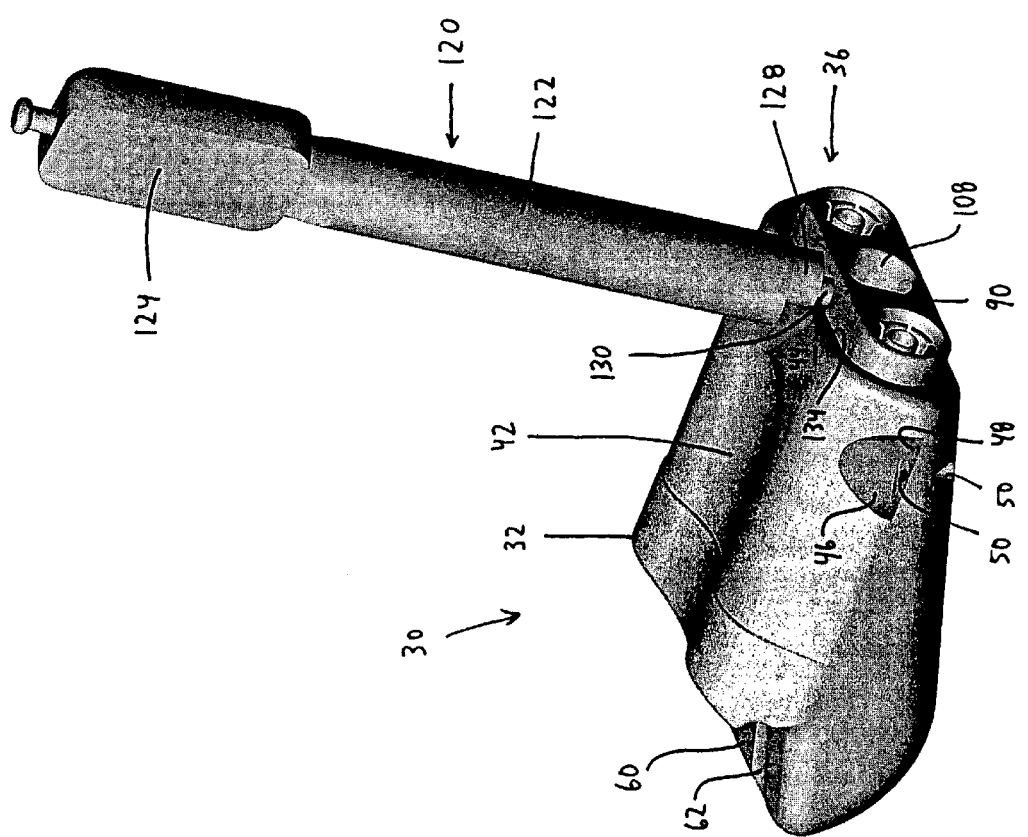
FIGS. 14 and 15 are perspective views of the device with the locking tool of FIGS. 9–12 applied thereto.
Figure 15:
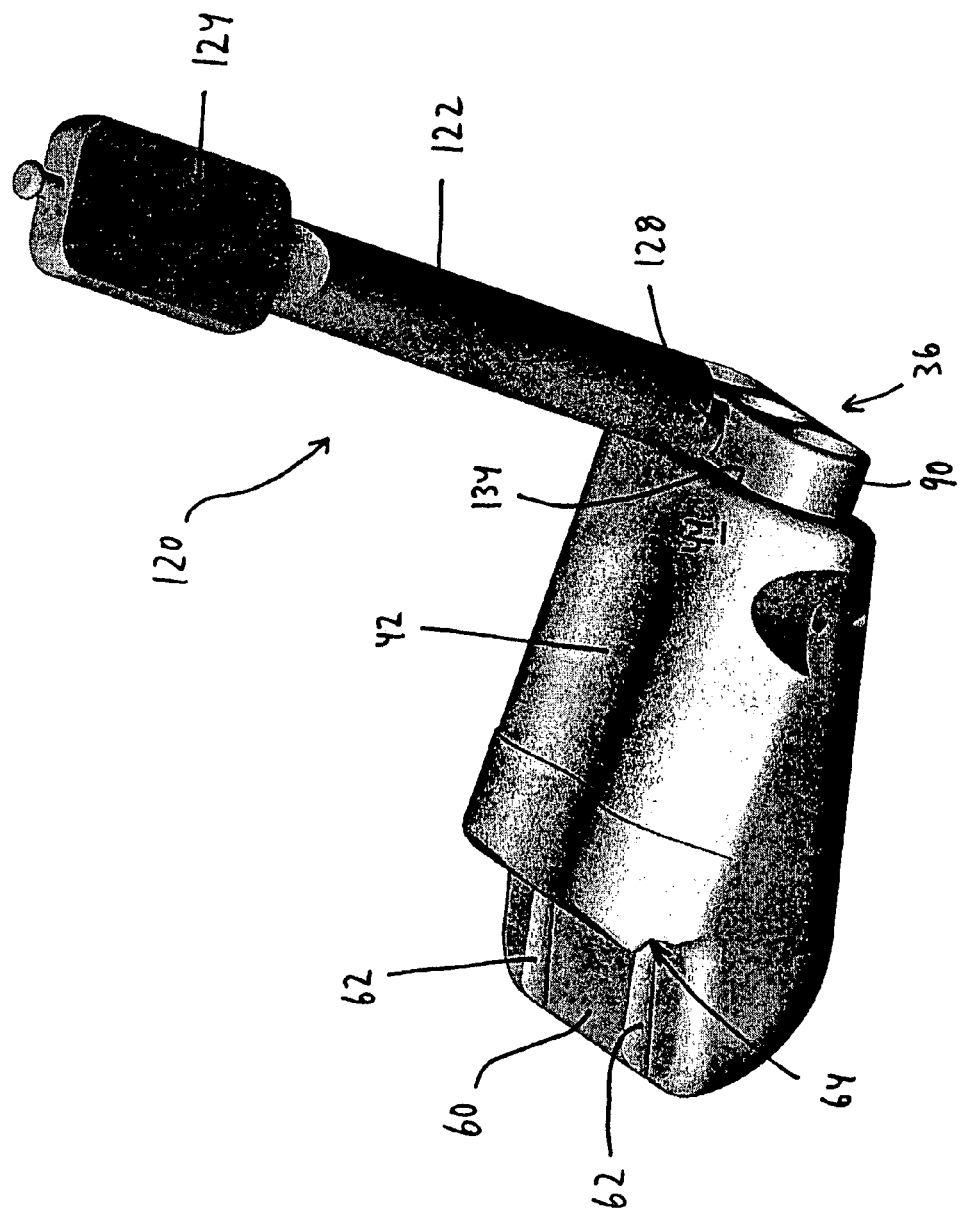
Figure 16:
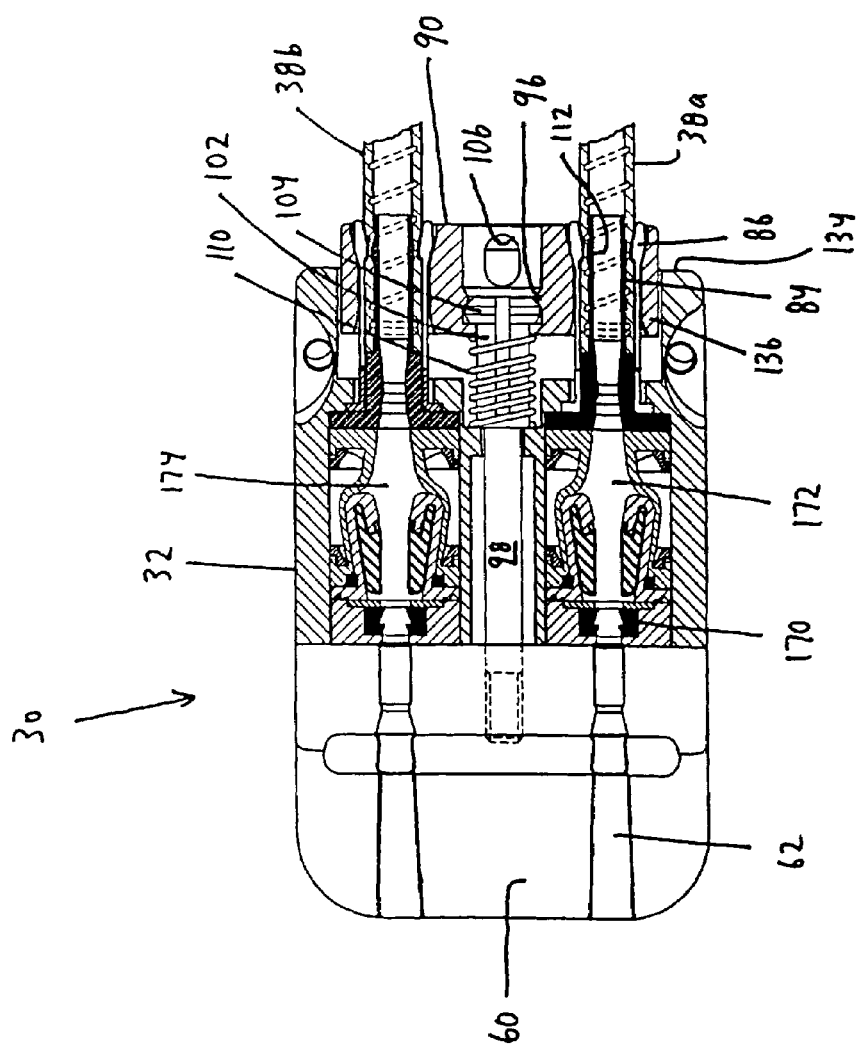
FIGS. 16 and 17 are similar to FIGS. 8 and 13, respectively, but showing the device and catheters locked together.
Figure 17:
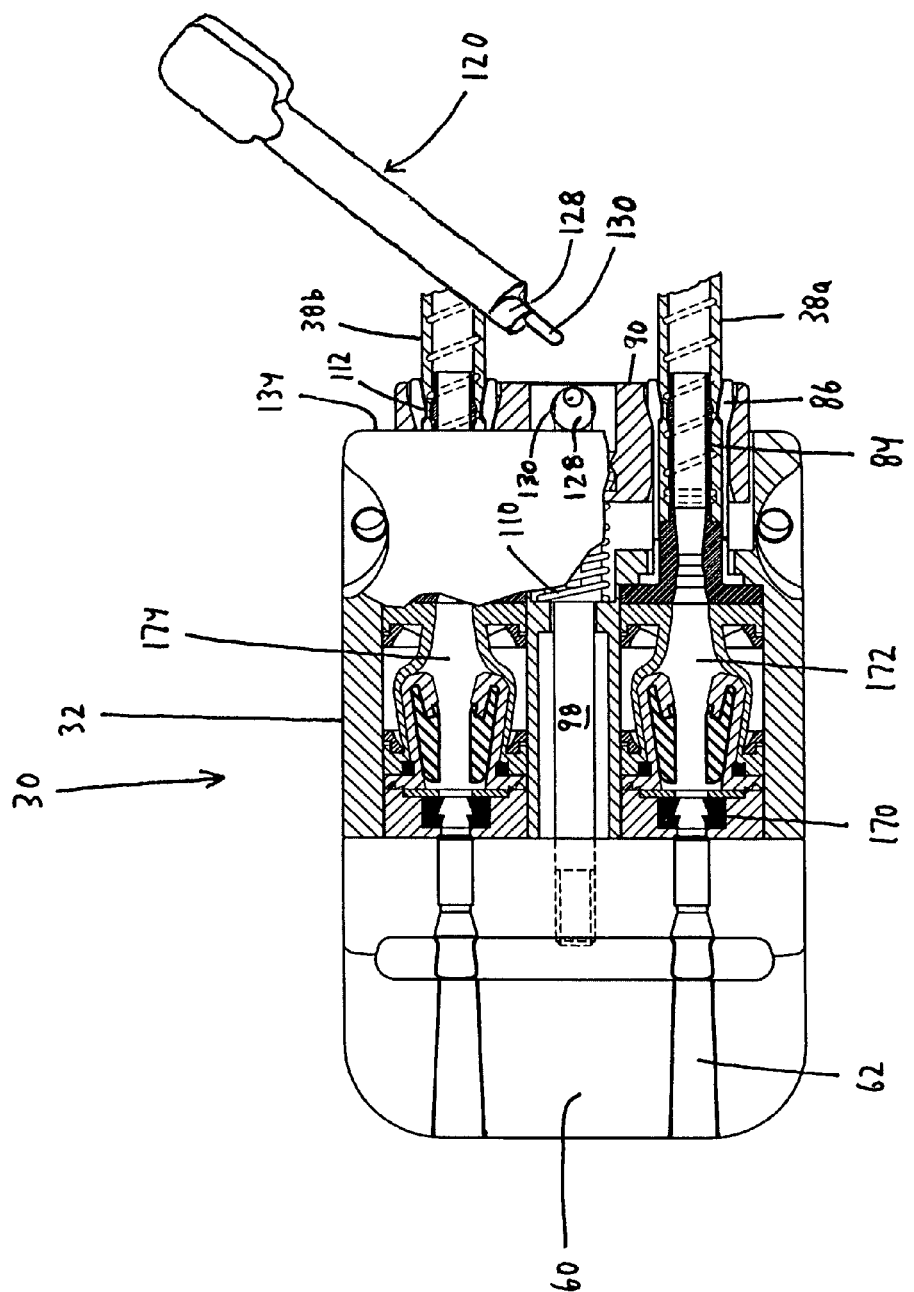

To effect locking of the catheters 38a and 38b to the device 30, the catheters are moved in the direction of arrows 132 (FIG. 13) into the annular spaces 88 between the tubes 84 and collets 86. The pin portion 130 of the locking tool 120 is inserted in the slot 106 in the lock member 90, with the cam portion 128 engaged with a distal wall 134 of the housing 32 (FIGS. 13–15). By grasping the flat handle 124 of the locking tool 120, an operator rotates the rod 122 and thereby the eccentric cam portion 128 and pin portion 130, causing the cam portion 128 to bear against the wall 134, such that the pin portion 130 bears against the distal end of the slot 106, urging the lock member 90 such that the flanges 104 and the legs 102 of locking bolt 98 are forced inwardly by the annular ridge 96. As the legs 102 flex inwardly toward one another, the ridge 96 overrides the flanges 104 and the lock member 90 moves from the position shown in FIG. 8 to the position shown in FIG. 16, with the lock member 90 fixed to the locking bolt 98 further distally on the bolt 98. Such movement of the lock member 90 causes inwardly-protruding cam portions 136 (FIG. 16) of the lock member 90 to engage and compress collets 86 against the catheters 38a, 38b, in turn compressing the catheters upon the outlet tubes 84.

Figure 22:
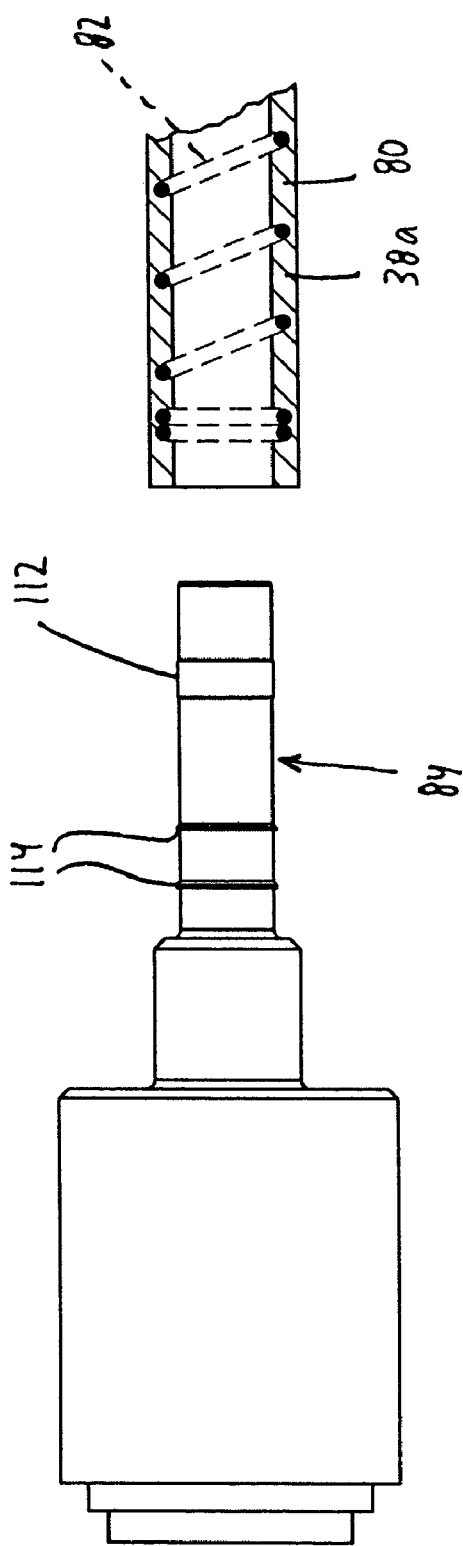
FIG. 22 is a side elevational view of a portion of the device and a portion of a catheter shown in section.

As shown in FIGS. 8, 13, 16, 17 and 22, the outlet tubes 84 may be provided with slightly enlarged bands 112 to increase gripping between the outlet tubes and the catheters 38a, 38b. In addition to, or in place of, the bands 112, the outlet tubes 84 may be provided with ribs 114 (FIG. 22). However, enlarged bands 112 and/or the ribs 114 are only modestly larger than the surrounding portions of the outlet tubes, so that the outer surfaces of the outlet tubes can form a smooth fit with the interiors of the catheters 38a, 38b without deforming the wire coils 82 of the catheters. It is possible to use such a construction, and still effectively secure the catheters to the outlet tubes, since collet-based lock means 36 are provided.

An unlocking tool 150, shown in FIGS. 18 and 19, is used in conjunction with the locking tool 120 to unlock the lock means 36, for separating the device 30 and the catheters 38a, 38b. The unlocking tool 150 includes a first planar portion 152. At a first end 154 thereof there is disposed a hook portion 156. At a second end 158 of first planar portion 152 there is disposed an aperture 160 extending through the first planar portion. Outwardly from the planar portion second end 158, a second planar portion 162 extends at an obtuse angle from the first planar portion 152.

Figure 20:
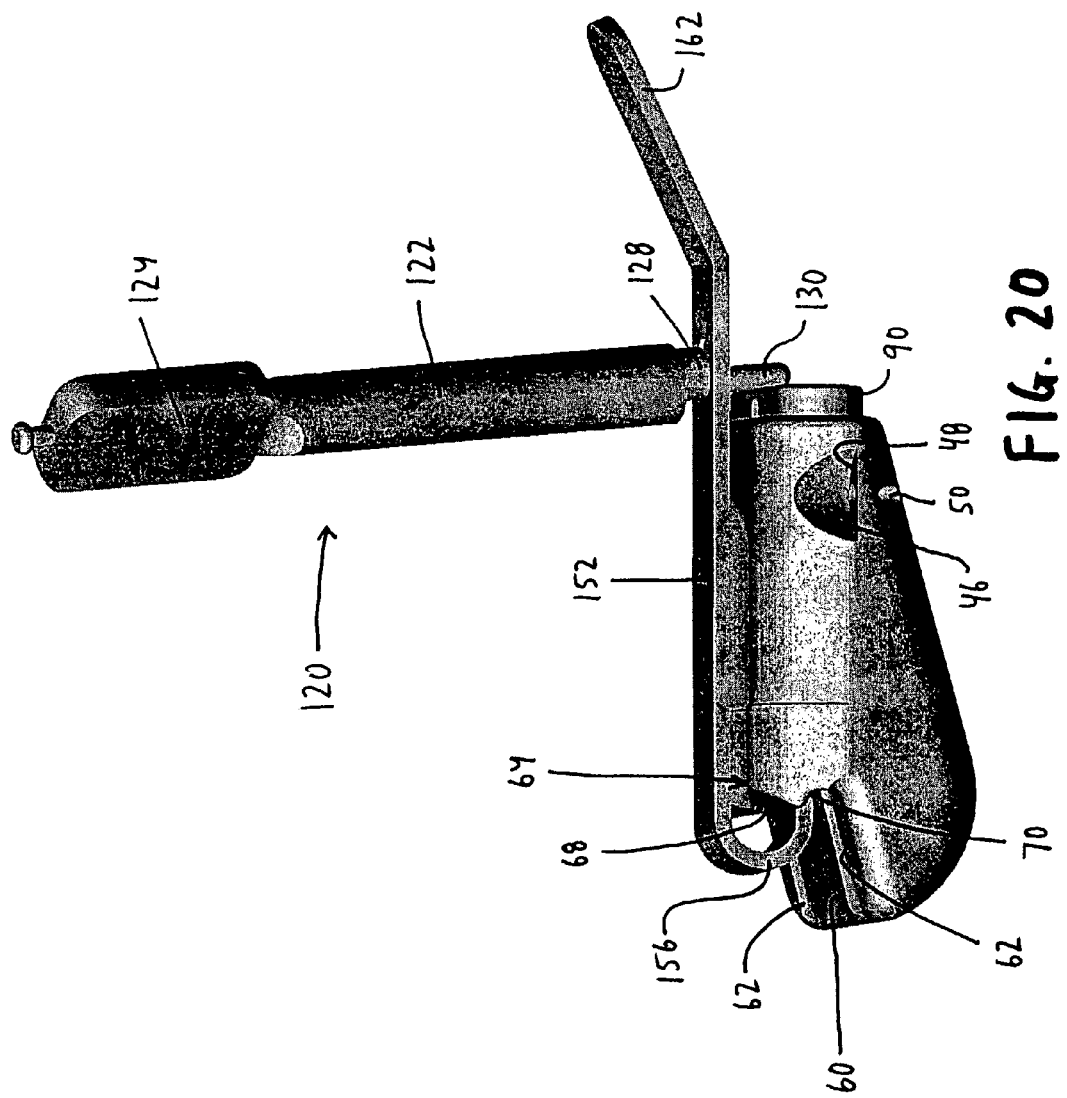
FIGS. 20 and 21 are perspective views of the device, with the unlocking tool of FIGS. 18 and 19 and the locking tool of FIGS. 9–12 applied to the device for a catheter unlocking operation.
Figure 21:
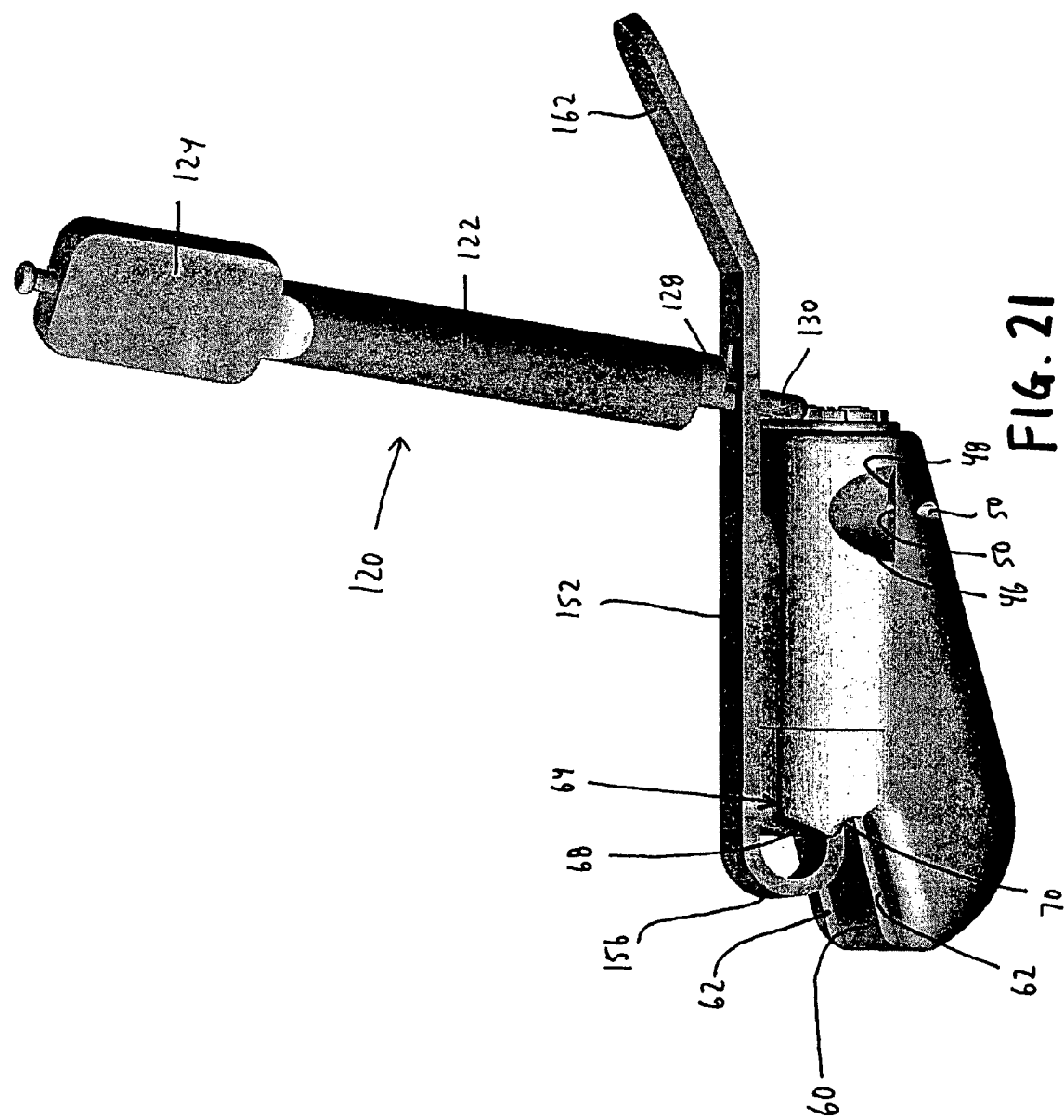

To unlock the lock means 36, the hook portion 156 of the unlocking tool 150 is placed on and around housing overhang 64, as shown in FIG. 20. The first planar portion 152 of the unlocking tool 150 is placed on the housing surface 44. The locking tool pin portion 130 is then extended through the unlocking tool aperture 160 until the locking tool cam portion 128 engages the unlocking tool first planar portion 152. By grasping the locking tool handle portion 124, the operator may lever the locking tool pin 130 against the lock member 90 to push the lock member 90 from the position shown in FIG. 16 to the position shown in FIG. 8, releasing locking pressure on the collets 86, and thereby releasing locking pressure on the catheters 36a, 36b, permitting the catheters to be removed from the outlet tubes 84. Referring to FIG. 19, it will be seen that the aperture 160 is configured to permit the locking tool pin to pivot in the aperture so as to provide leverage.

In FIGS. 8, 13, 16 and 17, there are shown seals 170 which receive the aforementioned incoming needles and serve to engage and retain the needles. In addition, there are shown internal components defining flow paths 172, 174. The seals 170 serve to retain the needles in the device 30. The flow path defining components serve to open and close the flow paths 172, 174, and also to retain the inserted needles. The structure and operation of the seals 170 and components defining the flow paths 172, 174 are described in detail in the aforementioned '956 patent application, incorporated herein by reference.

There is thus provided an improved port device having a profile which is more beneficially acceptable to body tissue and which permits tactile location of the needle entrances thereof, having needle receiving means which mechanically guide a needle from a point near the target entrance into the entrance, having a suturing facility within the device profile, and having means for securely locking reinforced catheters to the device and releasing the catheters to separate the device from the catheters. There are further provided specialized tools for performing the catheter locking and unlocking operations.

It is, of course, possible to modify the structure and use of the preferred embodiment disclosed above without departing from the scope of the present invention.

For example, in the preceding description, port device 30 as described as being disposed subcutaneously in the chest region of a patient. However, it could also be disposed in other regions of the patient with high flow vascular structures, such as femoral placement. In addition, port device 30 could also be used for peritoneal dialysis, with port placement in the abdomen of the patient and catheter access to the peritoneal cavity of the patient.

It is to be understood that the present invention is by no means limited to the particular constructions herein disclosed and/or shown in the drawings, but also comprises any modification or equivalent within the scope of the claims.

What is claimed is:

1. A port device for implanting in a patient for subcutaneous access to the vascular system of the patient, the device comprising a housing having needle receiving apparatus, and lock means for locking a catheter to the housing, said lock means comprising a collet for receiving the catheter when said collet is in an open condition, and a lock member responsive to application of a cam means to close said collet with the catheter therein, to lock the catheter in said collet and thereby in said housing;

wherein said device is provided with an outlet tube, said collet being disposed around the outlet tube to define an annular space therebetween adapted to receive the catheter, and the lock member being disposed around the collet, the lock member having inwardly directed cam protrusions, said lock member being movable by the cam means to cause the lock member protrusions to engage the collet, to cause the collet to engage the catheter which is thereby pressed against the outlet tube, to lock the catheter to the outlet tube; and wherein said device is provided with an internal lock bolt which is bifurcated to provide opposed legs, each of the opposed legs having a flange extending outwardly therefrom, the lock member having a bore therethrough, the lock bolt being disposed in the bore, the bore having an inwardly-extending ridge engaging the flanges and adapted to retain the flanges on a first side of the ridge to permit the lock member to remain in a position permitting the collet to remain in an open position and spaced from the outlet tube, the lock member being movable by the application of the cam means such that the inwardly-extending ridge causes inward movement of the opposed legs of the lock bolt, permitting the inwardly-extending ridge to override the flanges of the lock bolt and the flanges to reposition to a second side of the ridge to cause the lock member to engage the collet, causing the collet to engage the catheter disposed on the outlet tube, to press the catheter against the outlet tube to lock the catheter to the tube.

* * * * *